United States Patent [19]

Neti

[11] 4,268,370
[45] May 19, 1981

[54] HIGH TEMPERATURE, $CO_2$ INTERFERENCE FREE, ELECTROCHEMICAL $O_2$ SENSOR

[75] Inventor: Radhakrishna M. Neti, Brea, Calif.

[73] Assignee: Beckman Instruments, Inc., Fullerton, Calif.

[21] Appl. No.: 111,404

[22] Filed: Jan. 11, 1980

[51] Int. Cl.³ .............................................. G01N 27/46
[52] U.S. Cl. ................................. 204/195 P; 204/1 T
[58] Field of Search ................... 204/1 T, 1 P, 195 R, 204/195 P

[56] References Cited

U.S. PATENT DOCUMENTS

| | | | |
|---|---|---|---|
| 3,826,730 | 7/1974 | Watanabe et al. | 204/195 P |
| 3,856,636 | 12/1974 | Grubb | 204/195 P |
| 4,092,232 | 5/1978 | Zetter | 204/195 P |
| 4,185,620 | 1/1980 | Hagihara | 204/195 P |

OTHER PUBLICATIONS

Toni et al., "Lithium-Moist Air Battery", Globe-Union, Inc., Milwaukee, Wisconsin, (1966).

*Primary Examiner*—T. Tung
*Attorney, Agent, or Firm*—R. J. Steinmeyer; P. R. Harder; Robert S. Frieman

[57] ABSTRACT

An electrochemical sensor for determining the $O_2$ content of a fluid characterized in that the electrolyte employed therein is selected from a group consisting of amino alcohols having 2 to 12 carbon atoms, morpholine, and mixtures thereof. Optimally, the electrolyte can further comprise a supporting electrolyte selected from a group consisting of inorganic halides, organic supporting electrolytes, and mixtures thereof.

35 Claims, 6 Drawing Figures

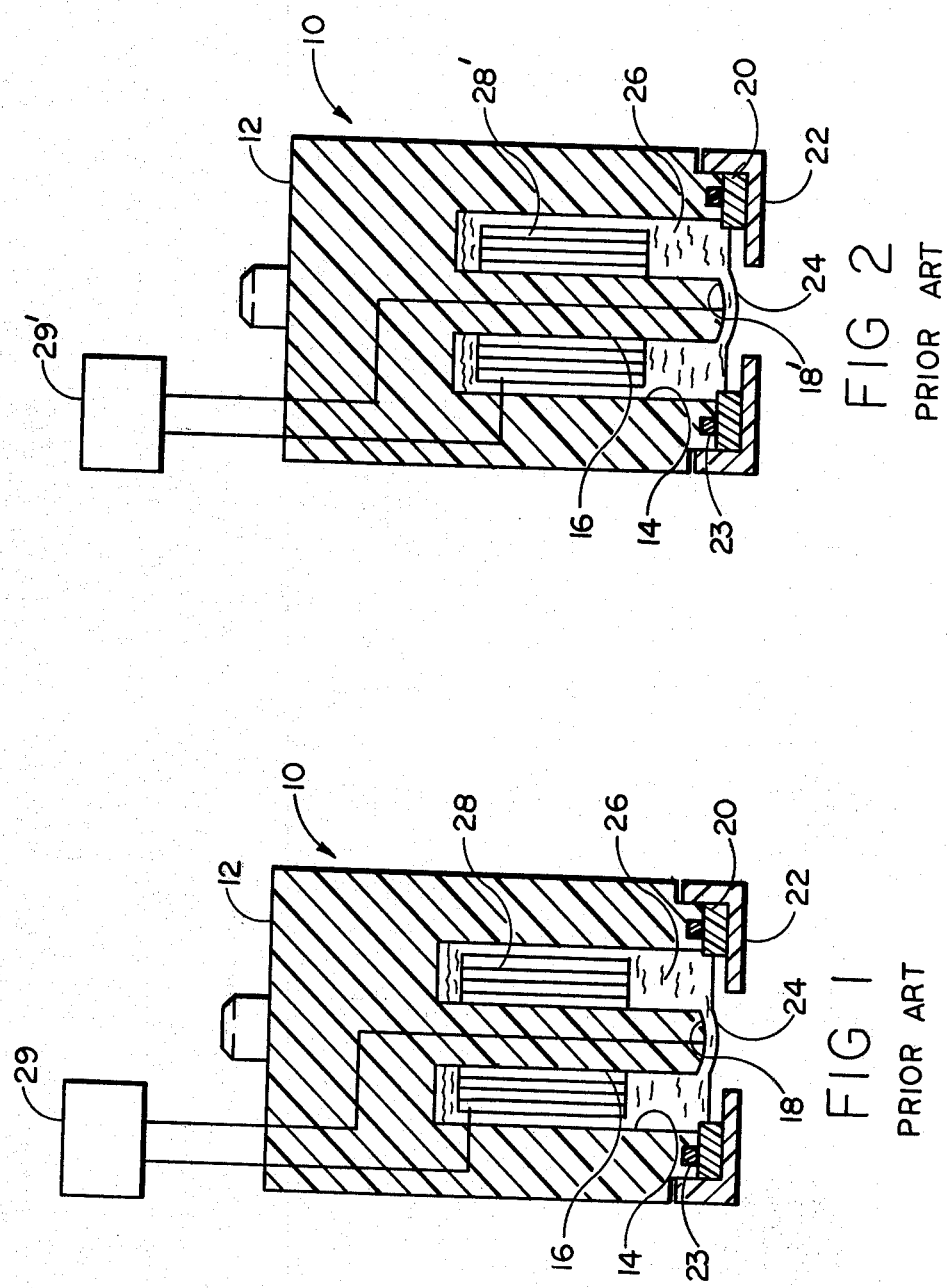

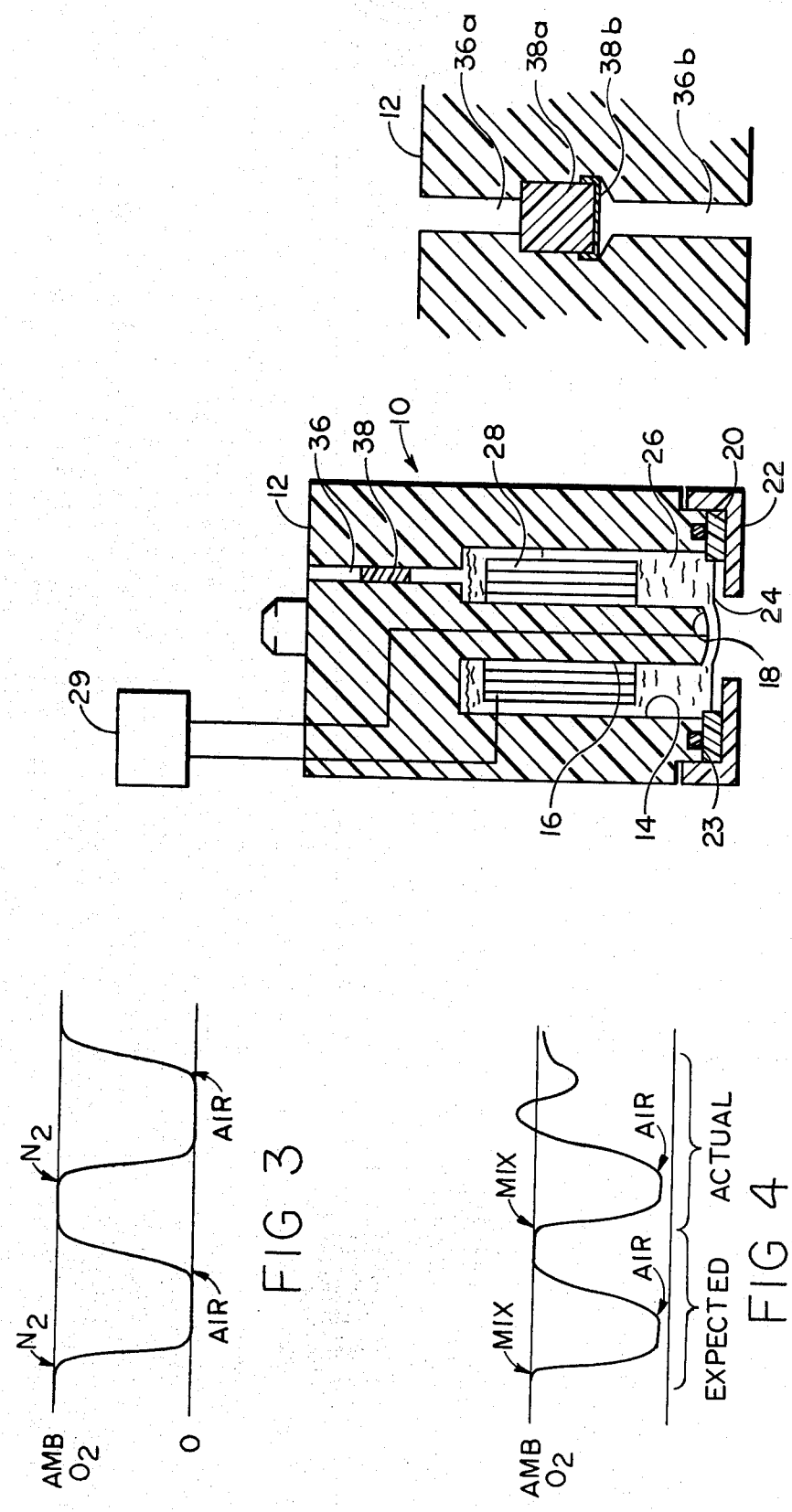

HIGH TEMPERATURE, $CO_2$ INTERFERENCE FREE, ELECTROCHEMICAL $O_2$ SENSOR

BACKGROUND OF THE INVENTION

1. Field of the Invention

The present invention relates to sensors capable of detecting a gas in a fluid and, more particularly, to sensors capable of measuring the presence and the amount of oxygen ($O_2$).

2. Description of the Prior Art

Analytical methods for the determination of $O_2$ in a fluid include the amperometric and galvanic methods. These methods are quite rapid, simple in operation, and are specially suited for determining $O_2$ in either its gaseous state or as it may be found dissolved in a liquid.

In the amperometric method, a sensor such as that shown in FIG. 1 is employed. In such a sensor, generally indicated as 10, body 12 is provided having a reservoir 14 therein containing a center post 16 for supporting a gold cathode 18. A membrane holder 20, cap 22, and O-ring 23 are provided to hold a polymeric membrane material 24, such as polytetrafluoroethylene of a thickness of from 0.00025 inches to 0.002 inches, stretched over the gold cathode thereby completely enclosing reservoir 14. Reservoir 14 is then filled with an electrolyte 26, typically a 5% KCl solution, either buffered or unbuffered. When the sensor is to be used in an application where temperatures in excess of 100° F. are generally encountered, the electrolyte is generally mixed with typical antifreeze compounds such as ethylene glycol. Additionally, an anode 28, typically silver, is disposed within reservoir 14 in contact with electrolyte 26. A potential of about 750 millivolts is applied between the anode 28 and the cathode 18 by means 29 connected thereto. In stretching the membrane 24 over cathode 18, a very minimal amount of electrolyte 26 is contained between gold cathode 18 and membrane 24. As sample fluid is brought in contact with membrane 24, $O_2$ diffuses through membrane 24 to contact the gold cathode 18 in the presence of the electrolyte 26. A current flow results which is linear with the partial pressure of $O_2$ being sampled. Thus, this current can be measured and correlated to the amount of $O_2$ in the sample.

In the galvanic method, a sensor such as that shown in FIG. 2 is employed, wherein corresponding numbers indicate corresponding parts. The sensor employed in the galvanic method typically has a silver cathode 18', a lead anode 28' and a readout device 29', e.g., an ammeter.

While these methods are satisfactory in many applications, they suffer drastically in atmospheres of high carbon dioxide ($CO_2$) such as encountered in monitoring automobile exhaust or stack gas emissions. Such sensors as that of FIG. 1 and FIG. 2, as described above, become less sensitive to $O_2$ upon even brief exposure to high concentrations of $CO_2$ and may take several hours to recover so as to indicate the proper value of $O_2$. The response of such sensors is highly dependent on the pH of the electrolyte at the interface between the gas diffusing through the membrane and the cathode. At low, or acid, pH levels the response is low. At high, or base, pH levels the response is higher. Typical responses by a prior art sensor are shown in FIG. 3 and FIG. 4. In FIG. 3, the sensor was first exposed to ambient air containing approximately 21% $O_2$. It was then exposed to pure nitrogen ($N_2$). FIG. 3 shows the response which was both expected and achieved. Upon exposure to $N_2$, the response dropped to the zero line. Upon exposure to air, the response climbed to the level indicating approximately 21% $O_2$. This cycle was repeatable without problem. Referring now to FIG. 4, the expected and actual response of a prior art sensor is shown when the sensor was exposed to ambient air and then exposed to a mixture of 15% $CO_2$ plus 3% $O_2$ and the balance nitrogen. When exposed to the mixture, the expected response is for the output to drop to the 3% level, being an indication of the 3% $O_2$ content of the mixture. Upon exposure to ambient air, it is expected that the output will climb to the 21% $O_2$ level of the ambient air. The actual response, however, was not as anticipated. When the sensor was exposed to the mixture, the response fell to the expected 3% $O_2$ level. When the sensor was subsequently exposed once again to the ambient air sample, the output overshot the 21% level, then reversed and undershot the 21% level, and then slowly approached the 21% level asymptotically. It was found that the recovery period required for the output to attain the actual 21% level varied depending both on the duration of exposure to $CO_2$ and the amount of $CO_2$ in the sample. For example, when using such a prior art sensor on an automobile exhaust, an exposure for a period one minute to the exhaust gases resulted in a recovery period on the order of two to three hours before an accurate ambient response could be attained.

This phenomenon is a result of the small volume of electrolyte trapped adjacent to the gold cathode by the membrane. This is typically on the order of 1 microliter. As previously mentioned, the response of such a cell is dependent on the pH of the electrolyte. When $CO_2$ is introduced, carbonic acid is formed which, when mixed with such an extremely small volume of basic electrolyte, results in a change of the pH of the electrolyte adjacent the gold cathode. In the typical electrolyte having a pH of approximately 13.5, the introduction of carbonic acid having a pH in the order of 4.5 results in a change of pH of the electrolyte trapped adjacent the gold cathode to a level of approximately 9. The response of the electrode will be correspondingly reduced until such time as the pH can attain its normal value by diffusion of normal electrolyte into the space between the membrane. The initial overshoot observed is, presumably, caused by the sudden change in pH and the unsettling of the electrolyte in the cathode area.

Attempts at improving the performance of $O_2$ sensors are not new in the art. It is well known that changes in pH of the electrolyte adjacent the cathode will change the response of the electrode. On the other hand, it is known that the thickness of the electrolyte in this same area affects the sensitivity of the electrode to oxygen. Thus, ideally, the spacing between the membrane and the cathode is kept minimal while means are provided for allowing the free movement of the electrolyte through the space. Thus, in the prior art, it has been suggested to roughen the surface of the gold cathode, provide channels therein for the movement of electrolyte, and depose porous materials between the membrane and the cathode to provide channels for the movement of the electrolyte.

Such prior art suggestions have resulted in $O_2$ sensors of marginal sensitivity and poor response times for certain applications. In particular, automobile exhaust analysis and flue gas analysis provide environments imposing restrictions beyond the capabilities of prior art $O_2$ sensors employing such techniques. In the field of automobile exhaust gas analysis, the ability to cycle and recover at rapid rates is imperative in "assembly line" type testing environments.

Accordingly, it would be highly desirable to have an electrochemical $O_2$ sensor capable of yielding accurate and reproducible date in applications wherein high $CO_2$ levels are encountered at both ambient, or low, and elevated temperatures. Such a sensor would be highly useful for monitoring the $O_2$ content of automobile exhaust and stack gas emissions.

SUMMARY OF THE INVENTION

According to the present invention, the problems characteristic of prior art electrochemical sensors are solved by the provision of an improved electrochemical sensor. The present electrochemical sensor is sensitive to the partial pressure of oxygen to a degree which allows it to be satisfactorily employed in critical applications such as automobile gas analysis and flue gas analysis while at the same time having a virtually instantaneous recovery rate following exposure to high levels of carbon dioxide concentration.

Briefly, the present invention encompasses an electrochemical $O_2$ sensor of the type including an electrode body forming a reservoir therein and having an opening at one end, a pair of electrodes mounted within the body and electrically connected by an electrolyte present in the reservoir, and a gas permeable membrane extending across the one end of the body and separating the electrodes and the electrolyte from a sample to be analyzed. The improved electrochemical $O_2$ sensor is characterized in that the electrolyte solution employed therein is selected from a group consisting of amino alcohols having 2 to 12 carbon atoms, morpholine, and mixtures thereof. Optionally, the electrolyte solution can further comprise a supporting electrolyte selected from a group consisting of inorganic halides, organic supporting electrolytes, and mixtures thereof.

Still other features, and attendant advantages of the present invention will become apparent to those skilled in the art from a reading of the following detailed description of the preferred embodiment, taken in conjunction with the accompanying drawings wherein like numerals designate like parts in the several figures.

BRIEF DESCRIPTION OF THE DRAWINGS

FIG. 1 is a cross section through an amperometric sensor according to the prior art.

FIG. 2 is a cross section through a galvanic sensor according to the prior art.

FIG. 3 is an illustration of the output of a prior art electrode when cycled between nitrogen and ambient air.

FIG. 4 is a drawing of the output, both expected and actual, of a prior art electrode being cycled between a mixture containing $CO_2$ and ambient air.

FIG. 5 is a cross section through an amperometric $O_2$ sensor according to a preferred embodiment of the present invention.

FIG. 6 is a partial cross section through an amperometric $O_2$ sensor according to a preferred embodiment of the present invention.

DESCRIPTION OF THE PREFERRED EMBODIMENT

The electrochemical $O_2$ sensor of the instant invention is characterized in that the electrolyte employed therein is selected from a group consisting of amino alcohols having from 2 to 12 carbon atoms, morpholine, and mixtures thereof. Amino alcohols suitable for use in the instant invention include, but are not limited to, 3-amino-1-propanol, 1-amino-2-propanol, and 2-amino ethanol. Amino alcohols which are also suitable for use in the instant invention but which are solid at ambient temperature and therefore need to be dissolved in a suitable material, e.g., water, include, but are not limited to, 2-amino-2-methyl-1,3-propanediol and 5-amino-1-pentanol.

More preferably, the electrolyte employed in the present invention is selected from the group consisting of 3-amino-1-propanol, 1-amino-2-propanol, 2-amino ethanol, morpholine, and mixtures thereof.

Preferably, the electrolyte solution also comprises a supporting electrolyte selected from a group consisting of inorganic halides, organic supporting electrolytes, and mixtures thereof. Although virtually any inorganic halide can be used as the supporting electrolyte in the instant invention, the inorganic halide preferably has a formula MX wherein M is selected from a group consisting of sodium, potassium, lithium, ammonium, and mixtures thereof and wherein X is selected from a group consisting of chlorine, bromine, iodine, and mixtures thereof.

Organic supporting electrolytes include, but are not limited to, tetraethyl ammonium perchlorate, tetraethyl ammonium fluoroborate, and mixtures thereof.

It is preferred that the electrolyte solution comprises from about 0.001 weight percent to saturation of the supporting electrolyte.

Optimally, the electrolyte is saturated with KCl.

When the electrode system of the instant invention is intended for use in normal ambient temperature applications (that is, about 60 to about 90° F.), the electrolyte solution can further comprise water without detrimentally affecting the efficacy thereof at these lower temperatures.

A preferred electrochemical $O_2$ sensor for use in conjunction with the electrolyte of the instant invention is shown in FIGS. 5 and 6. Referring now to FIG. 5, the preferred electrochemical $O_2$ sensor is substantially similar to the prior art electrochemical $O_2$ sensors described in connection with FIGS. 1 and 2 and the similar parts thereof will not be again described here. The preferred electrochemical $O_2$ sensor is, however, characterized in that it further comprises at least one opening 36 located in the body 12 of the sensor for permitting fluid communication between reservoir 14 and the atmosphere exterior to the body 12. A microporous composition 38 closes each of the openings 36. The incorporation of opening 36 and the microporous composition 38 in the sensor of the instant invention permits gas pressure in reservoir 14 to be maintained in equilibrium with the atmospheric pressure exterior thereto and thereby enables the $O_2$ sensor 10 to be used at elevated temperatures without adversely affecting its usefulness.

The porosity of the gas permeable microporous composition 38 is not critical but should be selected so that gases can freely pass therethrough without causing a buildup of pressure in the reservoir 14 of sensor 10. Some buildup of internal pressure can be tolerated provided that the amount of pressure buildup does not cause any stretching in the membrane 24 of the sensor 10. It is preferred that the porosity of the gas permeable microporous composition 38 be from about 0.1 to about 100 microns, more preferably from about 1 to about 50 microns.

The gas permeable microporous composition 38 can be selected from any of the numerous available compositions having the desired porosity. Examples of such compositions include, but are not limited to, metallic, plastic, and glass compositions. More particularly, the microporous composition 38 can be selected from a group consisting of porous stainless steel, porous sintered glass, porous polypropylene, porous polyvinylidene fluoride, porous polytetrafluoroethylene, porous polyethylene, and porous fluoroethylene propylene compositions. Preferably, the microporous composition 38 is selected from a group consisting of porous polyethylene, porous polyvinylidene fluoride, porous polytetrafluoroethylene, and porous fluoroethylene propylene compositions. Optimally, the gas permeable microporous composition 38 is selected from a group consisting of porous polyvinylidene fluoride, porous polytetrafluoroethylene, and porous fluoroethylene propylene compositions.

In a preferred embodiment of the $O_2$ sensor of the instant invention as illustrated in FIG. 6, the gas permeable microporous composition is comprised of a first gas permeable microporous member 38a and a second gas permeable microporous composition 38b wherein the second gas permeable microporous composition 38b has a porosity less than that of the first gas permeable microporous composition 38a. The second gas permeable microporous composition can be located either between the first gas permeable microporous composition 38a and the reservoir 26 as illustrated in FIG. 6 or between the first gas permeable microporous composition 38a and the atmosphere exterior to the body 12. Preferably, the second gas permeable microporous composition 38b is located between the first gas permeable microporous composition 38a and the reservoir 26.

When two gas permeable microporous compositions are employed in the sensor of the instant invention, the first gas permeable microporous composition 38a preferably has a porosity of from about 1 to about 100 microns and the second gas permeable microporous composition has a porosity of from about 0.1 to about 10 microns. Preferably, in such an arrangement, the first gas permeable microporous composition 38a has a porosity of from about 25 to about 50 microns and the second gas permeable composition 38b has a porosity of from about 1 to about 10 microns.

In this embodiment it is preferred that the first gas permeable microporous composition 38a be selected from a group consisting of porous polyvinylidene fluoride, porous fluoroethylene propylene, and porous tetrafluoroethylene compositions and that the second gas permeable microporous composition 38b be tetrafluoroethylene. Furthermore, it is preferred that the first gas permeable microporous composition have a porosity of about 35 microns and that the second gas permeable microporous composition have a porosity of about 5 microns.

It is also preferred that the cathode 18 employed in the instant invention have a surface radius of curvature of about 0.028 to about 0.03 inch. Furthermore, it is preferred that the surface of cathode 18 be finely polished, e.g., with a jeweler's rouge of 600 mesh or greater.

All materials conventionally used in the prior art to fabricate body 12, membrane 24, and O-ring 23 can be employed in the instant invention. However, due to the reactivity of electrolyte 26 employed in the instant invention, these parts, which are in contact with electrolyte 26, should preferably be manufactured from materials which are relatively chemically inert with respect to these electrolytes, e.g., glass, polyphenylenesulfide, polytetrafluoroethylene, quartz, and silicone.

The following examples are provided for the purpose of supporting the statements present in the above Background of the Invention section.

EXAMPLE 1

A sensor of the type shown in FIGS. 5 and 6 having a body fabricated from polyvinyl chloride was employed. This sensor was cleaned with alcohol to remove residual machine fluids therefrom and then dried in an oven to evaporate off all traces of the alcohol. The sensor was filled with an aqueous electrolyte consisting of 2% KOH and 5% KCl and then fitted with a fluoroethylene propylene (FEP) membrane having a thickness of 0.0005 inch. A perfluoroelastomeric O-ring was employed to hold the FEP membrane in place.

A 750 millivolt potential was applied from a Beckman Model 715 Oxygen Monitor and the output of the sensor when exposed to a constant oxygen concentration ($\sim 20.95\%$) was recorded on a strip chart recorder.

The sensor was first exposed to ambient air containing approximately 21% $O_2$. It was then exposed to pure $N_2$. FIG. 3 shows the response which was both expected and achieved. Upon exposure to $N_2$, the response dropped to the zero line and, upon exposure to air, the response climbed to the level indicating approximately 21% $O_2$. This cycle was repeatable without problem.

EXAMPLE 2

The same sensor employed in Example 1 was now exposed to ambient air and then exposed to a mixture comprising about 15% $CO_2$, about 3% $O_2$, and about 82% $N_2$. FIG. 4 shows the response which was both expected and achieved. When the sensor was exposed to the mixture, the response fell to the expected 3% $O_2$ level. However, when the sensor was subsequently exposed once again to the ambient air sample, the output overshot the 21% level, then reversed and undershot the 21% level, and then slowly approached the 21% level asymptotically.

The following examples are provided for the sole purpose of further illustrating the present invention and are not intended to be limitations thereon.

EXAMPLES 3–8

A sensor of the type shown in FIGS. 5 and 6 having a body fabricated from polyphenylenesulfide was employed. This sensor was cleaned with alcohol to remove residual machine fluids therefrom and then dried in an oven to evaporate off all traces of the alcohol. The sensor was filled with 2-amino ethanol and then fitted with an FEP membrane having a thickness of 0.0005 inch. A perfluoroelastomeric O-ring was employed to hold the FEP membrane in place.

A 750 millivolt potential was applied from a Beckman Model 715 Oxygen Monitor and the output of the sensor when exposed to a constant oxygen concentration ($\sim 20.95\%$) was recorded on a strip chart recorder. The data obtained therefrom is shown in Table I. This experiment, including the cleaning procedure, was repeated for each electrolyte listed in Table I.

TABLE I

| Example | Electrolyte | Response to $O_2$, µa |
|---|---|---|
| 3 | 2-amino ethanol | 0.4 |
| 4 | 3-amino-1-propanol | <0.1 |
| 5 | 1-amino-2-propanol | 1.65 |
| 6 | 2-amino ethanol saturated with KCl | 1.3 |
| 7 | 3-amino-1-propanol saturated with KCl | 1 |
| 8 | 1-amino-2-propanol saturated with KCl | 2.3 |

The data set forth in Table I evidences the fact that electrolytes within the scope of the instant invention can conduct an electrical current and therefore can be employed as an electrolyte to electrically connect the cathode and anode of an electrochemical sensor.

EXAMPLE 9

The sensor employed in Examples 3-8 was cleaned with alcohol and then dried in an oven to evaporate off all traces of alcohol. The sensor was filled with 2-amino ethanol and then fitted with an FEP membrane having a thickness of 0.0005 inch. A perfluoroelastomeric O-ring was employed to hold the FEP membrane in place.

A 750 millivolt potential was applied from a Beckman Model 715 Oxygen Monitor and the output of the sensor when exposed to a constant oxygen concentration (~20.95%) was recorded on a strip chart recorder. The data obtained therefrom is shown in Table II.

The sensor was then exposed for about 10 minutes to a mixture comprising about 15% $CO_2$, about 3% $O_2$, and about 82% $N_2$ while the output of the sensor was being recorded on the strip chart recorder. This data is also shown in Table II.

After being exposed to the above mixture, the sensor was again exposed to the constant oxygen concentration (~20.95%) and the data obtained from the strip chart recorder is set forth in Table II.

The sensor was then exposed to 100% $O_2$ and the data read off the strip chart recorder is shown in Table II.

TABLE II

| Exposed to | Strip Chart Recorder Reading, Divisions | % $O_2$ |
|---|---|---|
| ~20.95% $O_2$ | 126 | Cali.[1] |
| 3% $O_2$ + 15% $CO_2$ + 82% N2 | 20 | 3.32% |
| ~20.95% $O_2$ | 126 | 20.95 |
| ~100% $O_2$ | 601 | 99.93 |

[1]Cali. denotes calibration.

The data set forth in Table II demonstrates that an electrochemical $O_2$ sensor within the scope of the present invention is capable of yielding accurate and reproducible data in applications wherein high $CO_2$ levels are encountered. In addition, the data also shows that an electrode within the scope of the instant invention responds linearly to 100% $O_2$.

EXAMPLE 10

The sensor employed in Example 9 was placed in an oven having a constant oxygen gas concentration (20.95%) and the sensor's output was recalibrated. The sensor was maintained at equilibrium for at least 2-4 hours at each temperature range set forth in Table III. The data obtained from the experiment is set forth in Table III.

TABLE III

| Temperature, °C. | Strip Chart Recorder Reading, Divisions |
|---|---|
| 25 | 73 |
| 35 | 136 |
| 41-44 | 206 |
| 50 | 286 |
| 63-65 | 340 |
| 76-77 | 485 |
| 88-90 | 575 |
| 100-102 | 675 |

The data set forth in Table III demonstrate the temperature dependency of an amperometric $O_2$ sensor within the scope of this invention. In particular, th data depicts the expected change in output for any given oxygen concentration for an amperometric $O_2$ sensor exposed to various temperatures. For example, an amperometric $O_2$ sensor exposed to X% oxygen at about 101° C. is expected to have an output approximately twice that of the same sensor when exposed to the same X% oxygen concentration at about 64° C. Accordingly, the electrochemical $O_2$ sensor of this invention can be employed satisfactorily over a wide temperature range including both ambient, or low, as well as elevated temperatures.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. In an electrochemical sensor for determining the oxygen content of a fluid of the type comprising an electrode body forming a reservoir therein and having an opening at one end thereof, a cathode and anode mounted within said body, said cathode and anode being electrically connected by an electrolyte within said reservoir, a gas permeable membrane extending across said one end of said body and separating said cathode and anode and said electrolyte from a sample to be analyzed, the improvement comprising:
said electrolyte being selected from a group consisting of amino alcohols having from 2 to 12 carbon atoms, morpholine, and mixtures thereof.

2. The sensor of claim 1 wherein said electrolyte further comprises a supporting electrolyte selected from a group consisting of inorganic halides, organic supporting electrolytes, and mixtures thereof.

3. The sensor of claim 2 wherein said inorganic halide has a formula MX, wherein M is selected from a group consisting of sodium, potassium, lithium, ammonium, and mixtures thereof and wherein X is selected from a group consisting of chlorine, bromine, iodine, and mixtures thereof.

4. The sensor of claim 2 wherein said organic supporting electrolyte is selected from a group consisting of tetraethyl ammonium perchlorate, tetraethyl ammonium fluoroborate, and mixtures thereof.

5. The sensor of claim 2 wherein said inorganic halide has a formula MX, wherein M is selected from a group consisting of sodium, potassium, lithium, ammonium, and mixtures thereof, and wherein X is selected from a group consisting of chlorine, bromine, iodine, and mixtures thereof; said organic supporting electrolyte is selected from a group consisting of tetraethyl ammonium perchloriate, tetraethyl ammonium fluoroborate, and mixtures thereof; and said electrolyte solution comprises about 0.001 weight percent to saturation of said supporting electrolyte.

6. The sensor of claim 1 wherein said electrolyte is selected from a first group consisting of 3-amino-1-propanol, 1-amino-2-propanol, 2-amino ethanol, morpholine, and mixtures thereof; and a second group consisting of mixtures of (a) at least one member of said first group and (b) at least one member of a group consisting of 2-amino-2-methyl-1,3-propanediol and 5-amino-1-pentanol.

7. The sensor of claim 6 wherein said electrolyte further comprises a supporting electrolyte selected from a group consisting of inorganic halides, organic supporting electrolytes, and mixtures thereof.

8. The sensor of claim 7 wherein said inorganic halide has a formula MX, wherein M is selected from a group consisting of sodium, potassium, lithium, ammonium, and mixtures thereof and wherein X is selected from a group consisting of chlorine, bromine, iodine, and mixtures thereof.

9. The sensor of claim 7 wherein said organic supporting electrolyte is selected from a group consisting of tetraethyl ammonium perchlorate, tetraethyl ammonium fluoroborate, and mixtures thereof.

10. The sensor of claim 7 wherein said inorganic halide has a formula MX, wherein M is selected from a group consisting of sodium, potassium, lithium, ammonium, and mixtures thereof, and wherein X is selected from a group consisting of chlorine, bromine, iodine, and mixtures thereof; said organic supporting electrolyte is selected from a group consisting of tetraethyl ammonium perchlorate, tetraethyl ammonium fluoroborate, and mixtures thereof; and said electrolyte comprises about 0.001 weight percent to saturation of said supporting electrolyte.

11. The sensor of claim 1 wherein said electrolyte is selected from a group consisting of 3-amino-1-propanol, 1-amino-2-propanol, 2-amino ethanol, morpholine, and mixtures thereof.

12. The sensor of claim 11 wherein said electrolyte further comprises a supporting electrolyte selected from a group consisting of inorganic halides, organic supporting electrolytes, and mixtures thereof.

13. The sensor of claim 12 wherein said inorganic halide has a formula MX, wherein M is selected from a group consisting of sodium, potassium, lithium, ammonium, and mixtures thereof and wherein X is selected from a group consisting of chlorine, bromine, iodine, and mixtures thereof.

14. The sensor of claim 12 wherein said organic supporting electrolyte is selected from a group consisting of tetraethyl ammonium perchlorate, tetraethyl ammonium fluoroborate, and mixtures thereof.

15. The sensor of claim 12 wherein said inorganic halide has a formula MX, wherein M is selected from a group consisting of sodium, potassium, lithium, ammonium, and mixtures thereof, and wherein X is selected from a group consisting of chlorine, bromine, iodine, and mixtures thereof; said organic supporting electrolyte is selected from a group consisting of tetraethyl ammonium perchlorate, tetraethyl ammonium fluoroborate, and mixtures thereof; and said electrolyte comprises about 0.001 weight percent to saturation of said supporting electrolyte.

16. The sensor of claims 3, 5, 8, 10, 13, or 15 wherein MX is KCl and wherein said electrolyte is saturated with KCl.

17. The sensor of claim 1 wherein said electrolyte further comprises water.

18. The sensor of claim 17 wherein said electrolyte further comprises a supporting electrolyte selected from a group consisting of inorganic halides, organic supporting electrolytes, and mixtures thereof.

19. The sensor of claim 18 wherein said inorganic halide has a formula MX, wherein M is selected from a group consisting of sodium, potassium, lithium, ammonium, and mixtures thereof and wherein X is selected from a group consisting of chlorine, bromine, iodine, and mixtures thereof.

20. The sensor of claim 18 wherein said organic supporting electrolyte is selected from a group consisting of tetraethyl ammonium perchlorate, tetraethyl ammonium fluoroborate, and mixtures thereof.

21. The sensor of claim 18 wherein said inorganic halide has a formula MX, wherein M is selected from a group consisting of sodium, potassium, lithium, ammonium, and mixtures thereof, and wherein X is selected from a group consisting of chlorine, bromine, iodine, and mixtures thereof; said organic supporting electrolyte is selected from a group consisting of tetraethyl ammonium perchlorate, tetraethyl ammonium fluoroborate, and mixtures thereof; and said electrolyte comprises about 0.001 weight percent to saturation of said supporting electrolyte.

22. The sensor of claim 17 wherein said electrolyte is selected from a group consisting of 3-amino-1-propanol, 1-amino-2-propanol, 2-amino ethanol, morpholine, aqueous 2-amino-2-methyl-1,3-propaediol, aqueous 5-amino-1-pentanol, and mixtures thereof.

23. The sensor of claim 22 wherein said electrolyte further comprises a supporting electrolyte selected from a group consisting of inorganic halides, organic supporting electrolytes, and mixtures thereof.

24. The sensor of claim 23 wherein said inorganic halide has a formula MX, wherein M is selected from a group consisting of sodium, potassium, lithium, ammonium, and mixtures thereof and wherein X is selected from a group consisting of chlorine, bromine, iodine, and mixtures thereof.

25. The sensor of claim 23 wherein said organic supporting electrolyte is selected from a group consisting of tetraethyl ammonium perchlorate, tetraethyl ammonium fluoroborate, and mixtures thereof.

26. The sensor of claim 23 wherein said inorganic halide has a formula MX, wherein M is selected from a group consisting of sodium, potassium, lithium, ammonium, and mixtures thereof, and wherein X is selected from a group consisting of chlorine, bromine, iodine, and mixtures thereof; said organic supporting electrolyte is selected from a group consisting of tetraethyl ammonium perchlorate, tetraethyl ammonium fluoroborate, and mixtures thereof; and said electrolyte comprises about 0.001 weight percent to saturation of said supporting electrolyte.

27. The sensor of claim 17 wherein said electrolyte is selected from a group consisting of 3-amino-1-propanol, 1-amino-2-propanol, 2-amino ethanol, morpholine, and mixtures thereof.

28. The sensor of claim 27 wherein said electrolyte further comprises a supporting electrolyte selected from a group consisting of inorganic halides, organic supporting electrolytes, and mixtures thereof.

29. The sensor of claim 28 wherein said inorganic halide has a formula MX, wherein M is selected from a group consisting of sodium, potassium, lithium, ammonium, and mixtures thereof and wherein X is selected from a group consisting of chlorine, bromine, iodine, and mixtures thereof.

30. The sensor of claim 28 wherein said organic supporting electrolyte is selected from a group consisting of tetraethyl ammonium perchlorate, tetraethyl ammonium fluoroborate, and mixtures thereof.

31. The sensor of claim 28 wherein said inorganic halide has a formula MX, wherein M is selected from a group consisting of sodium, potassium, lithium, ammonium, and mixtures thereof, and wherein X is selected from a group consisting of chlorine, bromine, iodine, and mixtures thereof; said organic supporting electrolyte is selected from a group consisting of tetraethyl ammonium perchlorate, tetraethyl ammonium fluoroborate, and mixtures thereof; and said electrolyte comprises about 0.001 weight percent to saturation of said supporting electrolyte.

32. The sensor of claims 19, 21, 24, 26, 29, or 31 wherein MX is KCl and wherein said electrolyte is saturated with KCl.

33. The sensor of claims 1–15, 17–30 or 31 wherein said electrochemical device further comprises:
 (a) at least one means located in said body for permitting fluid communication between said reservoir and the atmosphere exterior to said body; and
 (b) a first gas permeable microporous composition closing each of said means, whereby gas pressure in said reservoir is maintained in equilibrium with the atmospheric pressure exterior thereto and thereby enabling said sensor to be used at elevated temperatures without adversely affecting the usefulness of said electrode.

34. The sensor of claims 1–15, 17–30 or 31 wherein said cathode has a surface radius of curvature of about 0.028 to about 0.03 inch, said surface being finely polished.

35. The sensor of claims 1–15, 17–30 or 31 wherein said electrochemical device further comprises:
 (a) at least one means located in said body for permitting fluid communication between said reservoir and the atmosphere exterior to said body; and
 (b) a first gas permeable microporous composition closing each of said means, whereby gas pressure in said reservoir is maintained in equilibrium with the atmospheric pressure exterior thereto and thereby enabling said sensor to be used at elevated temperatures without adversely affecting the usefulness of said electrode; and wherein said cathode has a surface radius of curvature of about 0.028 to about 0.03 inch, said surface being finely polished.

* * * * *